United States Patent
Wang et al.

(10) Patent No.: US 8,951,959 B2
(45) Date of Patent: Feb. 10, 2015

(54) GLUCAGON-LIKE PEPTIDE-1 ANALOGUES AND USES THEREOF

(75) Inventors: Yinxiang Wang, Beijing (CN); Fenlai Tan, Beijing (CN); Shaojing Hu, Beijing (CN); Xiangdong Zhao, Beijing (CN); Cunbo Ma, Beijing (CN); Yanping Wang, Beijing (CN); Xiaoyan Shen, Beijing (CN); Lieming Ding, Beijing (CN); Yunyan Hu, Beijing (CN); Hong Cao, Beijing (CN); Wei Long, Beijing (CN)

(73) Assignee: Betta Pharmaceuticals Co., Ltd., Hangzhou, Zhejiang (CN)

( * ) Notice: Subject to any disclaimer, the term of this patent is extended or adjusted under 35 U.S.C. 154(b) by 0 days.

(21) Appl. No.: 13/643,840

(22) PCT Filed: Apr. 29, 2011

(86) PCT No.: PCT/CN2011/000764
§ 371 (c)(1), (2), (4) Date: Oct. 26, 2012

(87) PCT Pub. No.: WO2011/134284
PCT Pub. Date: Nov. 3, 2011

(65) Prior Publication Data
US 2013/0053304 A1    Feb. 28, 2013

(30) Foreign Application Priority Data

Apr. 27, 2010  (CN) ............. 2010 1 0156732
Mar. 30, 2011  (CN) ............. 2011 1 0078365

(51) Int. Cl.
| | | |
|---|---|---|
| A61K 38/00 | (2006.01) | |
| A61P 9/10 | (2006.01) | |
| C07K 14/47 | (2006.01) | |
| A61P 3/04 | (2006.01) | |
| A61K 38/22 | (2006.01) | |
| A61P 3/08 | (2006.01) | |
| A61P 3/10 | (2006.01) | |
| A61K 38/26 | (2006.01) | |
| A61P 7/12 | (2006.01) | |
| C07K 14/605 | (2006.01) | |
| A61K 38/28 | (2006.01) | |
| C07K 5/00 | (2006.01) | |
| C07K 7/00 | (2006.01) | |
| C07K 16/00 | (2006.01) | |
| C07K 17/00 | (2006.01) | |

(52) U.S. Cl.
CPC .............. *C07K 14/605* (2013.01); *A61K 38/00* (2013.01)

USPC .............. 514/1.9; 530/308; 514/7.2; 514/5.3; 514/4.9; 514/11.7; 514/6.8

(58) Field of Classification Search
CPC ............................. C07K 14/605; A61K 38/00
See application file for complete search history.

(56) References Cited

U.S. PATENT DOCUMENTS

2009/0156478 A1 *  6/2009  Lau et al. .................. 514/12

OTHER PUBLICATIONS

Pipeleers et al "Restoring a functional B-cell mass in diabetes" Diabetes, Obesity and Metabolism 10 (Supplement 4):54-62. Published online Oct. 2, 2008.*
Wipf et al "Peptide-Like Molecules (PLMs): A Journey from Peptide Bond Isosteres to Gramicidin S Mimetics and Mitochondrial Targeting Agents" Chimia (Aarau) 63:764-775. Published Nov. 1, 2009.*
Green et al "Novel dipeptidyl peptidase IV resistant analogues of glucagon-like peptide-1(7-36)amide have preseved biological activities in vitro conferring improved glucose-lowering action in vivo" J Mol Endocrinol 31:529-540. Published 2003.*
Li et al "A novel GLP-1 analog, BPI3006, with potent DPP IV resistance and good glucoregulatory effect" Biochem Biophys Res Comm 400:563-568. Published online Sep. 6, 2010.*

* cited by examiner

*Primary Examiner* — James H Alstrum Acevedo
*Assistant Examiner* — Zachary J Miknis
(74) *Attorney, Agent, or Firm* — Weisun Rao; Greenberg Traurig, LLP

(57) ABSTRACT

Provided is a glucagon-like peptide-1 (GLP-1) analog shown as the following formula, wherein X is selected from glycine and glycinamide. The GLP-1 analog has a non-proteogenic amino acid residue in position 8 relative to the sequence GLP-1, and is acylated with a moiety comprising two acidic groups to the lysine residue in position 26. The GLP-1 analog is resistant to dipeptidyl peptidase IV so as to have an extended half-life in vivo. Also provided is a use of the GLP-1 analog in conquering blood sugar.

Figure 1:
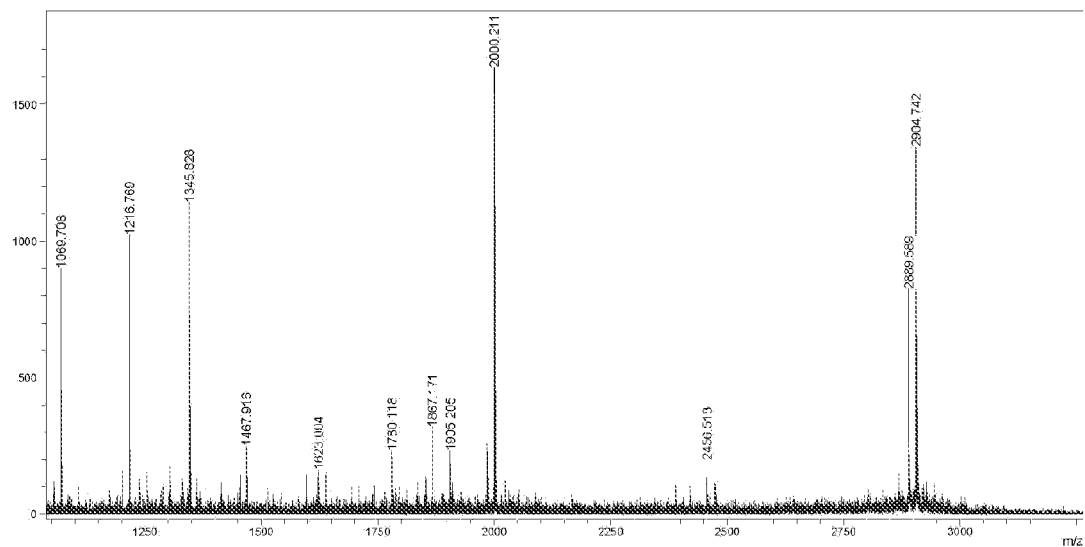

HOOC−(C)$_{15}$−Glu−N−O−O−N
H-His−N−CF$_3$−Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Arg-Gly-Arg-X

6 Claims, 2 Drawing Sheets

GLUCAGON-LIKE PEPTIDE-1 ANALOGUES AND USES THEREOF

CROSS REFERENCE TO RELATED APPLICATIONS

This application is a national phase application and claims the benefit, under 35 U.S.C. §371, of PCT/CN2011/000764, filed on Apr. 29, 2011, which in turn claims priority to CN 201110078365.2, filed on Mar. 30, 2011, and CN 201010156732.1, filed on Apr. 27, 2010. All of the priority applications are incorporated herein by reference in their entireties.

FIELD OF THE INVENTION

The present invention relates to glucagon-like peptide-1 analogues and use thereof.

BACKGROUND OF THE INVENTION

Diabetes has become the third ranked non-infectious disease after the cardiovascular and cerebrovascular diseases and tumors. WHO predicts that by year 2030, the population of diabetes patients worldwide will be more than 360 million, more than 90% of which are with type II diabetes. Type II diabetes refers to non-insulin-dependent diabetes mellitus or adult-onset diabetes, and is becoming more common. Type II diabetes is increasing at an alarming rate. Despite the advance in the treatment of diabetes, hypoglycemic episodes are often the limiting factor in achieving optimal blood sugar control. To address the limitation of current diabetes treatment, much progress has been made in the research of glucagon-like peptide-1 (Glucagon-like peptide-1, referred to as GLP-1). GLP-1 as gut hormone is secreted by intestinal L cells. It is a potent antihyperglycemic hormone inducing glucose-dependent stimulation of insulin secretion promote while suppressing glucagon secretion. GLP-1 appears to restore the glucose sensitivity of pancreatic β-cells, with the mechanism possibly involving the increased expression of GLUT2 and glucokinase. GLP-1 is also known to inhibit pancreatic β-cell apoptosis and stimulate the proliferation and differentiation of insulin-secreting β-cells. GLP-1 secretion plays an important role in the pathogenesis of type II diabetes. It has been reported that GLP-1 secretion from L-cells is reduced in patients with type II diabetes even though is still insulinotropic in T2DM have prompted several hypotheses about how this affects the estimated clinical effectiveness of these novel drugs. GLP-1 secretion by intestinal L cells in the circulation is dependent on the presence of nutrients in the lumen of the small intestine. The secretagogues (agents that cause or stimulate secretion) of this hormone include major nutrients like carbohydrate, protein and lipid. It is a potent antihyperglycemic hormone, inducing glucose-dependent stimulation of insulin secretion while suppressing glucagon secretion. Such glucose-dependent action is particularly attractive as novel diabetes treatment, because when the plasma glucose concentration is in the normal fasting range, GLP-1 no longer stimulates insulin to cause hypoglycemia.

The therapeutic potential for GLP-1 and its analogs is further increased if one considers its use in patients with type I diabetes. A number studies have demonstrated the effectiveness of native GLP-1 in the treatment of insulin dependent diabetes mellitus (IDDM). Similar to non-insulin dependent diabetes mellitus (NIDDM) patients, GLP-1 is effective in reducing fasting hyperglycemia through its glucagonostatic properties. Additional studies have indicated that GLP-1 also reduces postprandial glycemic excursion in IDDM, most likely through a delaying in gastric emptying. These observations suggest that GLP-1 may be useful as a treatment for IDDM as well as for NIDDM.

However, the biologic half-life of native GLP-1 molecules which are affected by the activity of dipeptidyl-peptidase IV (DPP IV) is quite short. For example, the biological half-life of GLP-1(7-37)OH is only 3 to 5 minutes. Sustained lowering of blood glucose concentration is only observed with continuous infusion, as demonstrated in studies in which GLP-1 was administered by intravenous infusion over a 24-hour period. Therefore extended-action GLP-1 based peptides that are resistant to DPP IV may have great therapeutic potential for treatment of diabetes mellitus.

BRIEF SUMMARY OF THE INVENTION

The present invention provides glucagon-like peptide-1 analogues and use thereof.

Firstly, the present invention provides compounds of Formula I, or pharmaceutically acceptable salts thereof, solvates thereof, chelates thereof, non-covalent complexes thereof, prodrugs thereof, or mixtures of any of the foregoing,

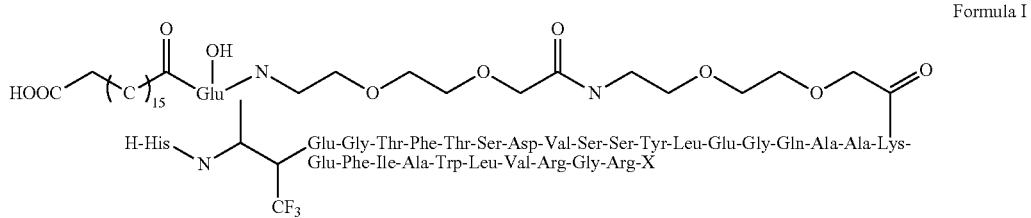

Formula I wherein X is glycine or glycinamide.

The present invention also provides pharmaceutical compositions each comprising a therapeutically effective amount of at least a compound of Formula I and at least one pharmaceutically acceptable excipient.

The present invention further provides the use of the pharmaceutical compositions for preparation of a medicament.

Preferably, the pharmaceutical compositions are used in preparation of medicaments for the treatment or prevention of type II diabetes, impaired glucose tolerance, type I diabetes, obesity, hypertension, syndrome X, dyslipidemia, cognitive disorders, atherosclerosis, myocardial infarction, coronary heart disease, cardiovascular disease, stroke, inflammatory bowel syndrome and/or dyspepsia or stomach ulcers.

Preferably, the pharmaceutical compositions are used in preparation of medicaments for delaying or preventing deterioration of type II diabetes.

Preferably, the pharmaceutical compositions are used in preparation of medicaments for decreasing food intake, decreasing β-cell apoptosis, increasing β-cell function, increasing β-cell mass and/or for restoring β-cells' sensitivity to glucose.

The present invention also provides the use of the compounds of Formula I for preparation of medicaments for the treatment or prevention of type II diabetes, impaired glucose tolerance, type I diabetes, obesity, hypertension, syndrome X, dyslipidemia, cognitive disorders, atherosclerosis, myocardial infarction, coronary heart disease, cardiovascular disease, stroke, inflammatory bowel syndrome, dyspepsia and/or gastric ulcers.

Preferably, the compounds of Formula I are used in preparation of medicaments for delaying or preventing deterioration of type II diabetes.

Preferably, the compounds of Formula I are used in preparation of medicaments for decreasing food intake, decreasing β-cell apoptosis, increasing β-cell function, increasing β-cell mass and/or for restoring β-cells' sensitivity to glucose.

The present invention further provides a method of modulating the blood glucose levels in a subject, which comprises administering to the subject a compound of Formula I.

The present invention is described in detail below and exemplified by the embodiments provided below.

Unless otherwise indicated, all numbers expressing quantities of different ingredients, reaction conditions, and so forth used in the specification and claims are to be understood as being modified in all instances by the term "rough" or "about". Accordingly, unless expressly indicated to the contrary, the numerical parameters set forth in the following specification and attached claims are approximations that may vary depending upon the standard deviation found in their respective testing measurements.

The compounds of the present invention may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan.

The compounds of Formula I include, but are not limited to, optical isomers of these compounds, racemates thereof, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, the compounds of Formula I include Z- and E-forms (or cis- and trans-forms) of compounds with double bonds. Where compounds of Formula I exist in various tautomeric forms, chemical entities of the present invention include all tautomeric forms of the compound.

The compounds of the present invention include, but are not limited to compounds of Formula I and all pharmaceutically acceptable forms thereof. Pharmaceutically acceptable forms of the compounds recited herein include pharmaceutically acceptable salts thereof, solvates thereof, crystal forms (including polymorphs and clathrates) thereof, chelates thereof, non-covalent complexes thereof, prodrugs thereof, and mixtures thereof. In certain embodiments, the compounds described herein are in the form of pharmaceutically acceptable salts thereof. As used henceforth, the term "compound" encompasses not only the compound itself, but also a pharmaceutically acceptable salt thereof, a solvate thereof, a chelate thereof, a non-covalent complex thereof, a prodrug thereof, and a mixture of any of the foregoing.

As noted above, prodrugs also fall within the scope of chemical entities, for example, ester or amide derivatives of the compounds of Formula I. The term "prodrugs" includes any compounds that become compounds of Formula I when administered to a patient, e.g., upon metabolic processing of the prodrug. Examples of prodrugs include, but are not limited to, acetate, formate, and benzoate and like derivatives of functional groups (such as alcohol or amine groups) in the compounds of Formula I.

At various places in the present specification, substituents of compounds of the invention are disclosed in groups or in ranges. It is specifically intended that the invention include each and every individual subcombination of the members of such groups and ranges. For example, the term "$C_{1-3}$ alkyl" is specifically intended to individually disclosed methyl, ethyl, and $C_3$ alkyl (including n-propyl and isopropyl).

The structure of Formula I as shown in the present invention provides compounds chemically stable, less susceptible to the body of dipeptidyl peptidase IV (DPP-IV) degradation of the plasma half-life of more than 30 hours, thereby overcoming the intravenous infusion of GLP-1 must continue to or continuous subcutaneous injection in order to effect a cure the defect. In addition, the present invention provides a structure as shown in compounds or the compounds as the active ingredient in the preparation of drugs used to lower blood glucose concentration, both a very long plasma half-life (30 hours), but also has a significant hypoglycemic effect.

BRIEF DESCRIPTIONS OF THE DRAWINGS

Figure 2:
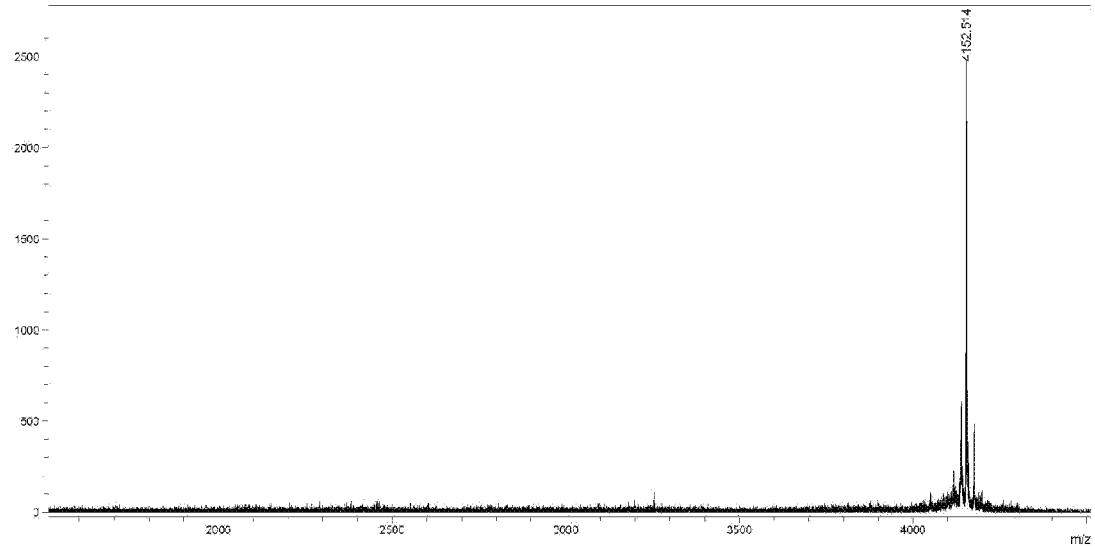
Figure 3:
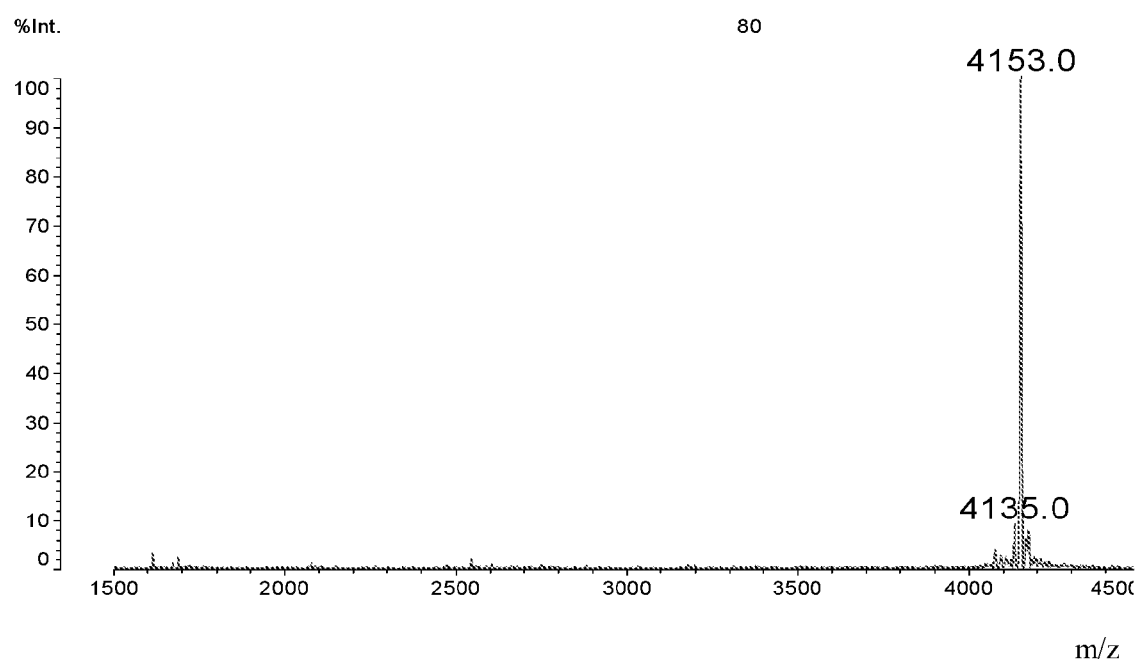

FIG. 1 shows MS of the compound of Formula II.
FIG. 2 shows MS of the compound of Example 1.
FIG. 3 shows MS of the compound of Example 2.

EMBODIMENTS OF THE INVENTION

The present invention is further exemplified, but not limited, by the following examples that illustrate the preparation of the compounds of Formula I of this invention.

The following examples only describes embodiments of the present invention so as to enable a person skilled in the relevant field of technology to carry it out, but shall not be interpreted to limit the scope of the present invention. In the examples below, some techniques or methods are not described in detail but are understood to be commonly known or used techniques or methods that are well within the skills of an artisan in the field to which the present invention relate.

Example 1

I. Synthesis of Intermediates (Dimer)

The structure of Dimer is shown below:

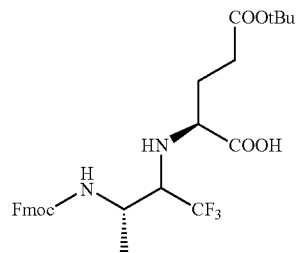

It can be synthesized in the following method:

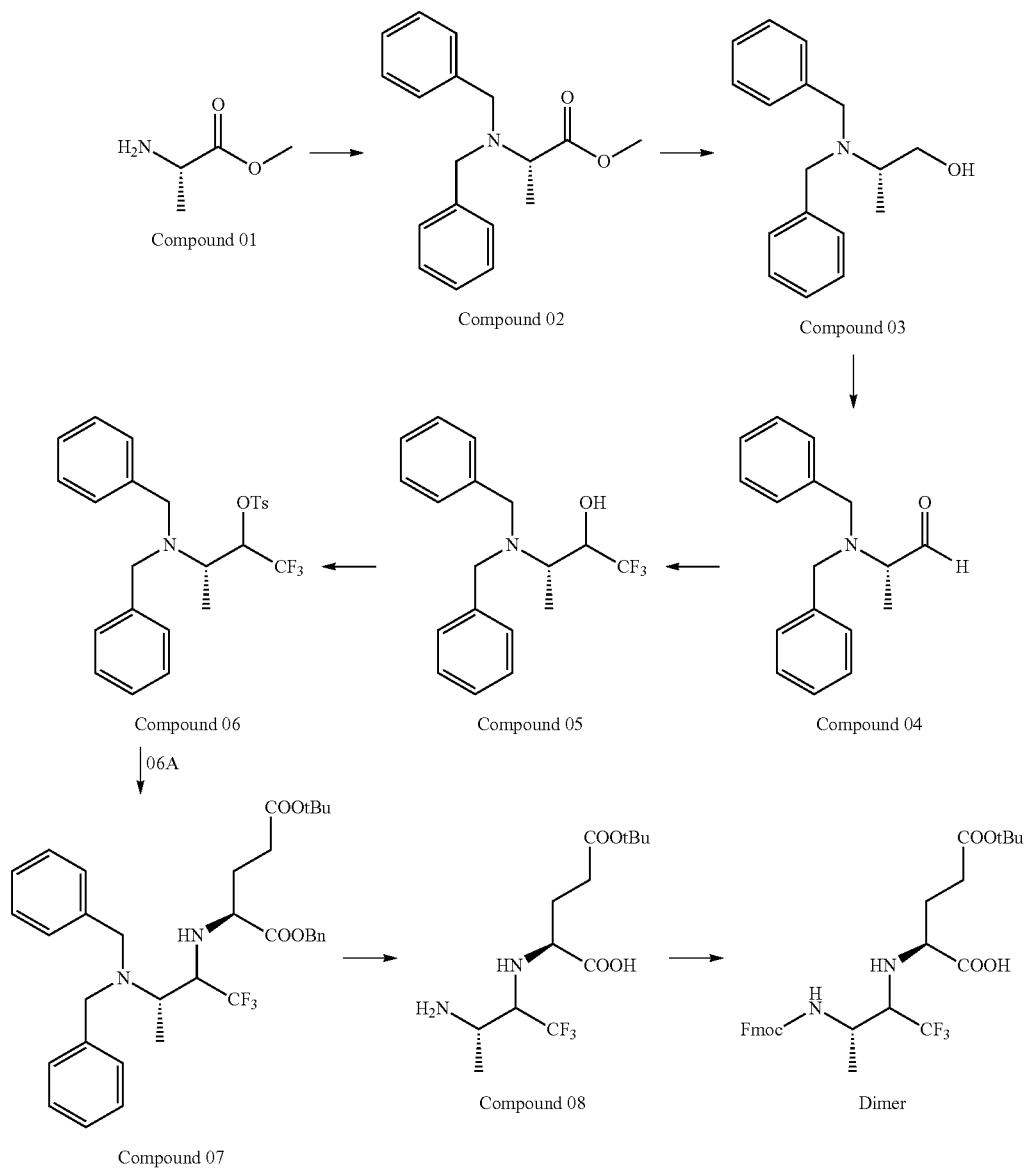

1. Preparation of Compound 01.HCl 80 mL of thionyl chloride was added dropwise to 250 mL of methanol at −10° C. within 2 hours. After the mixture was warmed to the room temperature and stirred for 1 hour, 40 g of L-alanine was added and stirred overnight. The reaction mixture was heated to reflux for 4 hours, cooled to the room temperature and concentrated to give 80 g of crude compound 01.HCl.

2. Preparation of Compound 02

113 g of benzyl bromide was added to the mixture of 40 g of compound 01.HCl in 350 mL of DMF. 150 g of anhydrous potassium carbonate was added to the above mixture, and stirring was continued for 2 hours. The reaction mixture was heated to 50° C. and stirred for 2 hours, cooled to the room temperature and extracted with 400 mL of ethyl acetate and 1200 mL of water. The organic layer was washed with 150 mL of 6N HCl, the aqueous phase was neutralized with sodium bicarbonate to pH 8 and extracted with ethyl acetate. The organic layers were dried with anhydrous magnesium sulfate and then concentrated to give a residue which was purified by column chromatography to give 57.6 g of Compound 02.

3. Preparation of Compound 03

A solution of 57.6 g Compound 02 in 100 mL ether was added dropwise to the mixture of 11.7 g of lithium aluminum hydride in 200 mL of diethyl ether within 1 hour at 0° C. The mixture was then warmed to 30° C. and reacted for 0.5 hours. 18 g of water was added dropwise to the reaction mixture within 1 hour at 0° C. to quench the reaction and the mixture was then stirred for 1 hour. Precipitation was removed by filtration and washed by ethyl acetate. All ethyl acetate was combined and concentrated under vacuum to give a residue which was purified in petroleum ether to give 36 g crystalline Compound 03.

4. Preparation of Compound 05

9.6 g of dimethyl sulfoxide in 50 mL of methylene chloride solution was added dropwise to a solution of 7.6 g of oxalyl chloride in 150 mL of dichloromethane within 0.5 hour at −65° C., then the mixture was stirred for 0.5 hour. To this mixture was added dropwise over an hour 11 g of Compound 03 in a 100 mL methylene chloride solution, and the solution was stirred for 1 hour. 14 g of triethylamine was added dropwise to the resultant solution within 1 hour and stirred for 2 more hours. The reaction mixture was warmed to the room temperature and then 50 mL water was added to the reaction mixture. The organic layer was separated and the aqueous phase was extracted with 50 mL of dichloromethane. The combined organic layers were washed with 100 mL saturated sodium bicarbonate and brine solution, followed by drying over anhydrous magnesium sulfate. The solvent was removed to obtain 11.7 g of Compound 04.

2.5 mL of TBAF in THF solution (1 mol/L) was added in a solution of Compound 04 in 150 mL of THF at 0° C., then TMSCF$_3$ in THF solution (9 g/50 mL) was added dropwise to the mixture and stirred for 15 minutes. 35 mL of concentrated HCl was added in the reaction mixture and stirred for 30 minutes. Then water and ethyl acetate was added to the reaction mixture and neutralized by sodium bicarbonate to pH 8. The organic layer was separated and dried over anhydrous magnesium sulfate. After concentration, the resultant residue was purified by flash chromatography on silica gel to give 9.0 g of Compound 05.

5. Preparation of Compound 06A

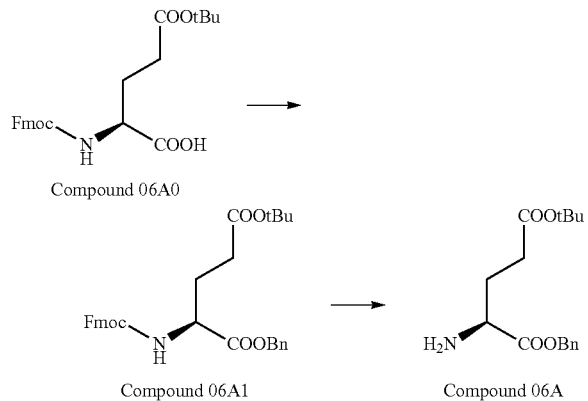

17.6 g of Compound 06A0 (commercially available) was dissolved in 200 mL of DMF, and to the solution were added 24 g of benzyl bromide and 36 g of sodium bicarbonate. The resultant mixture was stirred overnight. 1200 mL of water and 400 mL of ethyl acetate were then added to the mixture. The organic layer was separated, dried over anhydrous magnesium sulfate, and then concentrated to give a residue which was purified by column chromatography to give Compound 06A1.

A mixture of 75 mL of piperidine and 350 mL of ethyl acetate was added to Compound 06A1 with stirring for 2 hours at 25° C. The mixture was then concentrated to give a residue which was purified by column chromatography to give 10 g of Compound 06A.

6. Preparation of Compound 07

A sodium hydroxide solution (5 g/30 ml) was added at 0° C. to a 30 mL THF solution containing 2 g of Compound 05 and 0.2 g of TBAB. 2.5 g of p-toluenesulfonyl chloride was added to the solution and mixture was stirred for 30 minutes. Then water and ethyl acetate were added to the mixture. The organic layers were separated, dried, and concentrated to afford 2.7 g of Compound 06.

A 20 mL acetonitrile solution containing 2.7 g of Compound 06 and 3.3 g of Compound 06A was heated to reflux for overnight. Then acetonitrile was removed by evaporation and the resultant residue was washed with petroleum ether and separated by filtration. The filtrate was concentrated and the residue was purified by column chromatography to give 1.8 g of compound 07.

7. Preparation of Compound 08

0.3 g of Pd(OH)$_2$/C catalyst was added to a 400 mL methanol solution containing 1.8 g of Compound 07, and the mixture was hydrogenated overnight. The catalyst was filtered off and the methanol was concentrated to give 0.9 g of Compound 08.

8. Preparation of Dimer

A solution of Compound 08 (0.9 g) and FmocCl (0.9 g) in dioxane (40 mL) was stirred overnight. The reaction mixture was then filtrated to collect the precipitation and precipitation was washed with dioxane and petroleum ether to give 0.59 g of Dimer.

$^1$H NMR (DMSO-d$_6$): 1.04 (d, 3H), 1.38 (s, 9H), 1.50-1.91 (m, 2H), 2.21-2.30 (m, 2H), 3.06-3.08 (m, 1H), 3.30-3.37 (m, 1H), 4.26-4.38 (m, 4H), 7.32-7.46 (m, 4H), 7.72-7.76 (m, 2H), 7.90 (d, 2H), 8.04 (d, 1H).

$^{13}$C NMR (DMSO-d$_6$): 15.20, 20.46, 27.16, 30.55, 46.08, 48.88, 54.75, 55.12, 55.90, 65.66, 78.98, 119.54, 124.68, 124.79, 126.50, 126.75, 127.11, 140.21, 143.07, 143.24, 156.02, 171.37, 174.69.

$^{19}$F NMR (DMSO-d$_6$): 70.023.

LC-MS m/z: 551 (M+H).

II. Synthesis of Main Chain

1. Swelling.

Fmoc-Gly-Wang Resin (0.27 mmol/g, 0.2 mol) was kept in DCM for 20 minutes and then the resin was collected by filtration.

2. Deprotection of Fmoc.

The above resin was added to a 10 mL solution of PIPE/DMF (PIPE/DMF=1/4) and kept in the solution for 8-10 minutes, then the mixture was filtrated to collected the resin.

The following ninhydrin-based Kaiser Test (KT test) was conducted to detect free amino-group: 30-50 granules resin was washed with DCM for 3 times. After three reagents (A, B and C) was added about 2 drops each, the mixture was kept at 115° C. for 5 minutes. The deprotection was considered to be completed when both the solution and the resin turned blue.

3. Washing.

The resin was washed by DCM and DMF each for 6 times and then filtrated.

4. Coupling.

DIC is a preferred choice for the coupling reaction. It was conducted as follows: A 5 mL DMF solution containing Fmoc-Arg(Pbf)-OH (0.8 mmol, 0.52 g), HOBt (0.8 mmol, 0.11 g) and DIC (0.8 mmol, 125 µL) was stirred for 1.5 hours. The procedure for detecting free amino-group through KT test was then employed: 30-50 granules resin was taken out and then washed with DCM for 3 times. After three reagents (A, B and C) was added about 2 drops, the mixture was kept at 115° C. for 5 minutes. The reaction was considered to be completed when both the solution and resin turned to light yellow or colorless. The reaction was uncompleted when the solution or resin was still light blue, and the detection procedure was repeated for additional 3 hours. Uronium type coupling reagent (amino acid/HATU/HOAt/DIEA=1/0.95-0.98/1/2) was employed when the reaction was still uncompleted after the three hours.

5. Capping

When a peptide of up to 20 amino acids in total and KT tests revealed the presence of unreacted amino functions after recoupling, it was necessary to cap these to avoid the formation of deletion sequences. Capping was realized through a short treatment (15 minutes at the room temperature) of the resin with a solution of acetic anhydride and DIEA (1:3 in molar ratio) in the resin:reagent ratio of 1:5, followed by filtration to dry.

6. Washing

The resin was washed with DCM, followed by DMF and this washing step was repeated 5 times and dried by filtration.

7. Steps 2-6 were repeated to complete the synthesis of the main chain.

8. As for the side chain on the Lys(12) of a peptide, the selective deprotection (i.e., a protecting group in one molecule can be removed of selectively without affecting other protecting groups) was needed. Fmoc-Lys (Dde)-OH could be chosen because it was needed to use amino protecting group that could not be removed by PIPE. The coupling method using diisopropylcarbodiimide carbodiimide (DIC method), as described above under Example 1.4, was followed.

9. A peptide of Formula II was obtained after the main chain with Thr(25) on the C-terminal was cleaved. Its molecular weight was confirmed by MS (cal. 2905.18. found 2904.74), as shown FIG. 1.

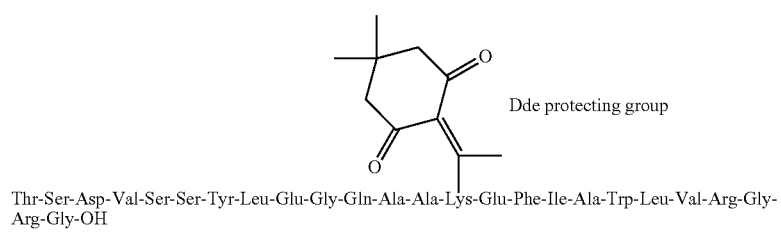

Formula II

Dde protecting group

Thr-Ser-Asp-Val-Ser-Ser-Tyr-Leu-Glu-Gly-Gln-Ala-Ala-Lys-Glu-Phe-Ile-Ala-Trp-Leu-Val-Arg-Gly-Arg-Gly-OH

10. A compound of this invention has an amino acid at position 29 from the C-terminal in the main chain (Dimer, with its structure shown above). Its amino group was protected by Fmoc and its carboxyl group was protected by OtBu. It was obtained by coupling, with di-isopropyl carbodiimide as the coupling reagent. Specifically, Dimer (0.55 g, 1.0 mmol, 5 equiv of resin), HOBt (0.14 g, 1 mmol), and di-isopropyl carbodiimide (DIC) (160 µL, 1 mmol) in 5 mL DMF were added to the resin and the reaction was continued at the room temperature for 3 hours to couple Dimer to the main chain.

11. Coupling of the last C-terminal amino acid (His) was completed by coupling of Boc-His (Trt)-OH and using diisopropyl carbodiimide (DIC) as the coupling agent or a uronium type coupling reagent.

III. Synthesis of Side Chain and Connecting to Main Chain

1. The side chain, as shown in Formula III, is a compound of this invention. It has the sequence of octadecanedioic acid-γ-Glu-AEEA-AEEA, wherein C*OOH is linked to the main peptide chain shown in Formula II. The protecting Dde group (i.e., 1-(4, 4-dimethyl-2,6-dioxocyclohexylidene)ethyl) on Lys(12) of the main peptide chain of Formula II was removed by 2% hydrazine. The side chain was coupled to the Lys by the same procedure as described above under 11.2-6. The synthesis of the side chain shown in Formula III was completed by coupling Fmoc-AEEA-OH and Fmoc-Glu-OtBu and uronium type coupling reagents used to link the γ-carboxyl group of Glu to the amino group of AEEA, followed by the final coupling of 1,18-octadecanedioic acid with one carboxyl group protected by tBu.

IV. Cleaving and Purification

1. Cleavage

The peptide resin was washed and dried by filtration. Its cleavage was performed by using ratio of 1 g of peptide-resin with 10 ml Lysates. Specifically, the peptide resin was added to a solution of Lysates (TFA:TA:EDT:$H_2O$:phenol=82.5:5:2.5:5:5) and stirred for 3 hours. The mixture was diluted with ice-cooled 500 mL of ether and the precipitate was collected by centrifuge. The precipitate was then washed for 4 times and air dried to give crude compound of Formula I.

2. Purification

Crude compound of Formula I was dissolved in 90% methanol/water. The solution was treated with ultra sound and then filtered through a 0.45 µm ultrafiltration membrane. The filtrate was purified by preparative chromatography to give pure compound of Formula I. The MS analysis showed the correct molecular weight (cal. 4152.1. found 4152.5), as shown in FIG. 2.

Example 2

The synthesis of the main peptide chain of Formula II was conducted by the use of Rink Amide Resin instead of Fmoc-Gly-Wang Resin. The other conditions were the same as described in Example 1.

Unless otherwise specified, the temperature referred to in Example 1 and Example 2 was the room temperature. Reagents A, B and C were 80% phenol in ethanol solution, redistilled pyridine, and a ninhydrin/ethanol solution (5 g in 100 mL).

Example 3

Oral Glucose Tolerance Test (OGTT)

1. Groups

90 ICR (Institute of Cancer Research) mice, all male, were divided into three batches by body weight, with each batch having 30 mice. After fasting and overnight, each batch was divided into two groups based on the blood sugar level: the Vehicle group and the group receiving the compound of Example 1 ("Compound group"). The Vehicle group was treated with saline only, and the Compound group was treated with Compound of Example 1 dissolved in saline.

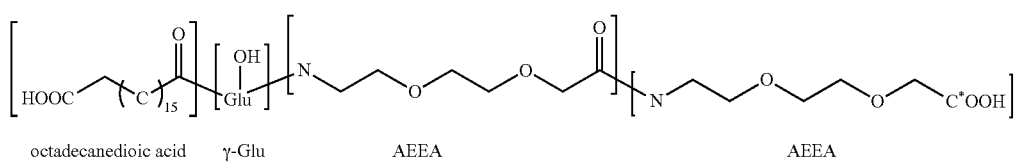

Formula III octadecanedioic acid    γ-Glu    AEEA    AEEA

2. Experiments

Batch 1:

The mice were divided into two groups based on their blood sugar level after fasting overnight. On Day 1, they were administered with saline or the Compound in saline (0.3 mg/kg) by subcutaneous injection. 2 hours after the administration, the mice were gavaged with a dose of glucose (2 g/kg) and their blood samples were taken from the tip of the tail 30 minutes and 60 minutes after the glucose administration. Their blood glucose levels were measured. On Day 4 (72 hours after test compound administration), following an overnight fast, both mouse groups were gavaged with a dose of glucose (2 g/kg). Blood samples were taken 30 minutes after the glucose administration and the blood glucose level was measured.

Batch 2:

The mice were divided into groups based on their blood sugar level after fasting overnight. On Day 1, the mice were administered with the test compound by subcutaneous injection at the dosage of 0.3 mg/kg. On Day 2, after fasting for 8 hours, the mice were gavaged with a dose of glucose (2 g/kg) and their blood samples were taken 30 minutes after the glucose administration and the blood glucose level was measured. Another glucose gavage was performed on Day 5 (90 hours after test compound administration) following an overnight fast and the blood glucose levels 30 minutes after glucose administration were measured.

Batch 3:

The mice were divided into groups based on their blood sugar level after fasting overnight. On Day 1, the mice were administered with the test compound by subcutaneous injection at the dosage of 0.3 mg/kg. On Day 3, after fasting overnight, the mice were gavaged with a dose of glucose (2 g/kg, 42 hours after the administration of test compound) and their blood samples were taken 30 minutes after the glucose administration and the blood glucose level was measured.

Measurement of the blood glucose level was conducted with Roche's ACCU-CHEK® integrated blood glucose detection system.

3. Results (1) 2 hours after compound administration

| Group | Dose (mg/kg) | Blood Glucose (mM) | | | Blood Glucose (% versus FBG) | | |
|---|---|---|---|---|---|---|---|
| | | FBG | 30 min | 60 min | FBG | 30 min | 60 min |
| Vehicle | | 2.88 ± 0.48 | 8.73 ± 2.27 | 7.12 ± 2.93 | 100.0 | 311.9 ± 100.3 | 255.0 ± 111.6 |
| Compound | 0.3 | 2.93 ± 0.64 | 4.87 ± 2.33 | 3.40 ± 1.31 | 100.0 | 159.7 ± 44.6 | 115.5 ± 31.5 |

(2) 25 hours after compound administration

| Group | Dose (mg/kg) | Blood Glucose (mM) | | | Blood Glucose (% versus FBG) | | |
|---|---|---|---|---|---|---|---|
| | | FBG | 0 min | 30 min | FBG | 0 min | 30 min |
| Vehicle | | 3.03 ± 0.65 | 7.23 ± 0.69 | 10.73 ± 1.83 | 100.0 | 247.3 ± 50.7 | 373.0 ± 119.5 |
| Compound | 0.3 | 2.92 ± 0.50 | 4.25 ± 0.30 | 7.12 ± 1.14 | 100.0 | 149.2 ± 25.8 | 250.6 ± 59.3 |

(3) 42 hours after compound administration

| Group | Dose (mg/kg) | FBG | PBG | 0 min | 30 min |
|---|---|---|---|---|---|
| | | Blood Glucose (mM) | | | |
| Vehicle | | 3.08 ± 0.63 | 9.18 ± 1.68 | 4.17 ± 0.94 | 9.87 ± 2.53 |
| Compound | 0.3 | 2.92 ± 0.35 | 7.57 ± 0.38 | 3.67 ± 0.80 | 5.53 ± 1.27 |
| | | Blood Glucose (% versus FBG) | | | |
| Vehicle | | 100.0 | 308.4 ± 85.0 | 138.0 ± 35.6 | 323.1 ± 85.2 |
| Compound | 0.3 | 100.0 | 262.0 ± 26.4 | 125.9 ± 22.0 | 193.2 ± 53.3 |

PBG: Postprandial blood glucose measured before fasting.

(4) 72 hours after compound administration

| Group | Dose (mg/kg) | FBG | PBG | 0 min | 30 min |
|---|---|---|---|---|---|
| | | Blood Glucose (mM) | | | |
| Vehicle | | 2.88 ± 0.48 | 8.47 ± 0.88 | 4.78 ± 1.26 | 9.60 ± 1.44 |
| Compound | 0.3 | 2.93 ± 0.64 | 7.33 ± 0.52 | 3.17 ± 0.63 | 6.82 ± 2.71 |
| | | Blood Glucose (% versus FBG) | | | |
| Vehicle | | 100.0 | 299.0 ± 47.6 | 168.4 ± 46.6 | 341.7 ± 79.5 |
| Compound | 0.3 | 100.0 | 258.6 ± 51.3 | 111.0 ± 29.8 | 234.0 ± 91.2 |

(5) 90 hours after compound administration

| Group | Dose (mg/kg) | FBG | PBG | 0 min | 30 min |
|---|---|---|---|---|---|
| | | Blood Glucose (mM) | | | |
| Vehicle | | 3.03 ± 0.65 | 9.15 ± 1.04 | 3.10 ± 0.09 | 13.43 ± 1.53 |
| Compound | 0.3 | 2.92 ± 0.50 | 7.80 ± 0.46 | 3.55 ± 0.47 | 8.78 ± 0.88 |

-continued

| Group | Dose (mg/kg) | FBG | PBG | 0 min | 30 min |
|---|---|---|---|---|---|
| | | Blood Glucose (% versus FBG) | | | |
| Vehicle | | 100.0 | 315.5 ± 79.1 | 105.5 ± 19.2 | 462.3 ± 120.2 |
| Compound | 0.3 | 100.0 | 276.6 ± 65.5 | 123.7 ± 19.8 | 307.8 ± 54.8 |

The data above indicate that the test compound has significant ability to reduce the blood glucose level and was able to do so for 90 hours after its administration.

Further, the compounds of this invention have a plasma half-life of over 30 hours, while the plasma half-life of GLP-1 is 1-2 minutes.

It is understood that the embodiments described above are merely illustrative examples of this invention and do not constitute the scope of this invention which is defined by the accompanying claims. Various modifications or changes to the invention made by a person skilled in the art, without departing from the essence of this invention, are all to be included within the scope of this invention.

The invention claimed is:

1. A compound of Formula I,

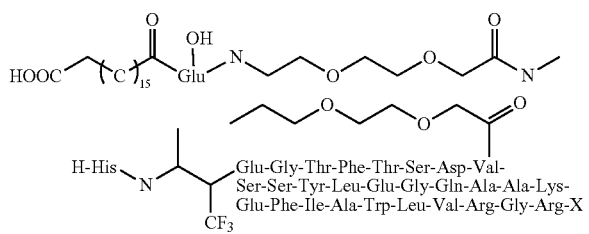

or a pharmaceutically acceptable salt thereof, wherein X is glycine or glycinamide.

2. A pharmaceutical composition comprising a therapeutically effective amount of at least one compound of claim 1 and at least one pharmaceutically acceptable excipient.

3. A method of modulating the blood glucose level in a subject in need thereof comprising administering to the subject a compound of claim 1.

4. A method for treating a disease, disorder, or condition in a subject thereof, comprising administering to the subject in need thereof a therapeutically effective amount of a compound of claim 1, wherein the disease, disorder, or condition is type diabetes, impaired glucose tolerance, type I diabetes, obesity, hypertension, or syndrome X.

5. A method for treating or delaying a disease, disorder, or condition in a subject thereof; comprising administering to the subject in need thereof a therapeutically effective amount of a compound of claim 1, wherein the disease, disorder, or condition is type II diabetes.

6. A method for decreasing food intake, decreasing β-cell apoptosis, increasing β-cell function, increasing β-cell mass and/or for restoring glucose sensitivity to the β-cells in a subject, comprising administering to the subject in need thereof a therapeutically effective amount of a compound of claim 1.

* * * * *

UNITED STATES PATENT AND TRADEMARK OFFICE
CERTIFICATE OF CORRECTION

| | | |
|---|---|---|
| PATENT NO. | : 8,951,959 B2 | Page 1 of 1 |
| APPLICATION NO. | : 13/643840 | |
| DATED | : February 10, 2015 | |
| INVENTOR(S) | : Yinxiang Wang et al. | |

It is certified that error appears in the above-identified patent and that said Letters Patent is hereby corrected as shown below:

Title page, item 57 in the abstract, change the structure of Formula I to

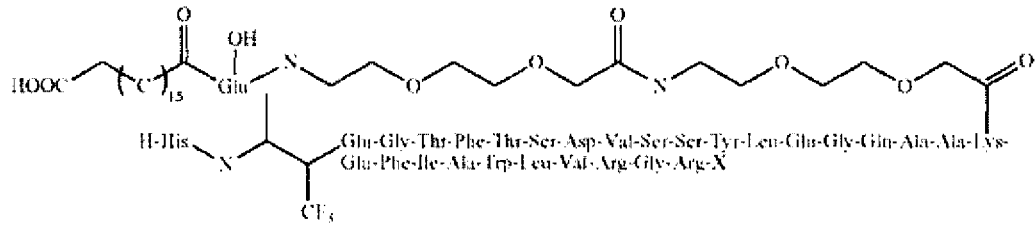

In the Specification
In Column 2, line 37, "Formula I" should appear under the chemical structure.
In Column 9, line 46, change "11.2-6" to "II.2-6".
In Column 10, line 8, "Formula II" should appear under the chemical structure.
In Column 10, line 52, "Formula III" should appear under the chemical structure.

In the Claims
In Column 13, line 15, Claim 1, change the structure of Formula I to

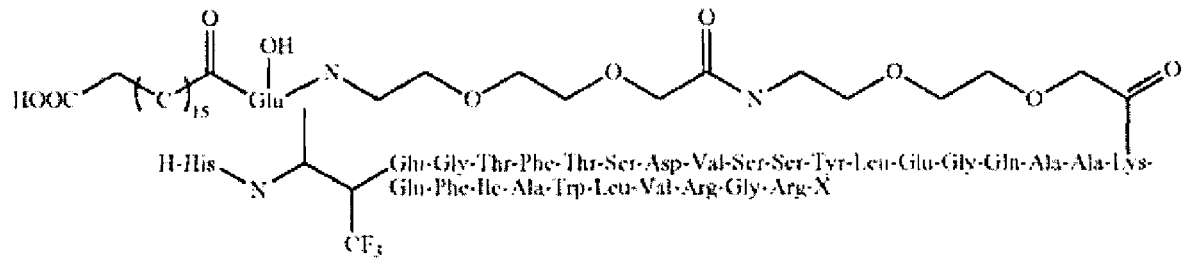

In Column 14, Line 13, Claim 4, change "type diabetes" to "type II diabetes".

Signed and Sealed this
Thirtieth Day of June, 2015

Michelle K. Lee
*Director of the United States Patent and Trademark Office*